United States Patent
Connor et al.

(10) Patent No.: US 11,340,133 B2
(45) Date of Patent: May 24, 2022

(54) SYSTEM AND METHOD OF DETECTING GAS-LEAKAGE ALONG AN UNDERGROUND PIPELINE SYSTEM

(71) Applicants: Sidney Allen Connor, Columbiana, OH (US); Grant Hammer, Stonewall, LA (US)

(72) Inventors: Sidney Allen Connor, Columbiana, OH (US); Grant Hammer, Stonewall, LA (US)

( * ) Notice: Subject to any disclaimer, the term of this patent is extended or adjusted under 35 U.S.C. 154(b) by 134 days.

(21) Appl. No.: 17/033,560

(22) Filed: Sep. 25, 2020

(65) Prior Publication Data

US 2021/0088405 A1 Mar. 25, 2021

Related U.S. Application Data

(60) Provisional application No. 62/905,797, filed on Sep. 25, 2019.

(51) Int. Cl.
| | |
|---|---|
| *G01M 3/04* | (2006.01) |
| *F17D 5/02* | (2006.01) |
| *G01M 3/24* | (2006.01) |
| *G01N 7/00* | (2006.01) |
| *G01N 33/00* | (2006.01) |

(52) U.S. Cl.
CPC .............. *G01M 3/243* (2013.01); *G01N 7/00* (2013.01); *G01N 33/0063* (2013.01)

(58) Field of Classification Search
CPC ............ G01M 3/00; G01M 3/04; G01M 3/08; G01M 3/243; G01N 7/00; G01N 33/00; G01N 33/0063; F17D 5/00–04
See application file for complete search history.

(56) References Cited

U.S. PATENT DOCUMENTS

| | | | | | |
|---|---|---|---|---|---|
| 319,364 | A | * | 6/1885 | Westinghouse, Jr. | |
| 327,703 | A | * | 11/1885 | McElroy | |
| 10,928,372 | B2 | * | 2/2021 | McMillan | G08B 21/12 |

FOREIGN PATENT DOCUMENTS

| | | | | | |
|---|---|---|---|---|---|
| CN | 107676632 | A | * | 2/2018 | F17D 5/00 |
| CN | 109099321 | A | * | 12/2018 | F01D 15/10 |
| GB | 341440 | A | * | 1/1931 | |
| GB | 2176604 | A | * | 12/1986 | G01M 3/243 |
| KR | 101663490 | B1 | * | 10/2016 | F17D 5/02 |

\* cited by examiner

*Primary Examiner* — Nguyen Q. Ha

(57) ABSTRACT

A system and method of detecting gas leakage along an underground pipeline system accurately determines the presence of a gas leak while minimizing cost and preserving energy. The system includes at least one underground pipeline with a plurality of stack vents, a plurality of sensor units, and at least one remote server. Each sensor unit is mounted within a stack vent. The method begins by tracking a current time with each sensor unit. A gas-concentration reading with at least one specific unit is captured and then communicated along with a sensor location and a sensor identification to the remote server and recorded with the remote server. The tracking, capturing, and communicating of the gas-concentration reading is repeated so that actual gas-concentration data is compiled and compared to a baseline gas-concentration data or a defined gas-concentration threshold. A leak notification for a gas leak is then sent with the remote server.

13 Claims, 15 Drawing Sheets

SYSTEM AND METHOD OF DETECTING GAS-LEAKAGE ALONG AN UNDERGROUND PIPELINE SYSTEM

The current application claims a priority to the U.S. provisional patent application Ser. No. 62/905,797 filed on Sep. 25, 2019.

FIELD OF THE INVENTION

The present invention generally relates to methods of gas leak detection. More specifically, the present invention efficiently detects gas-leakage along an underground a pipeline system.

BACKGROUND OF THE INVENTION

Natural gas, which is treated as an alternative to the depleting supplies of oil, is widely used for fuel and electricity production. Natural gas consumption has been increasing steadily in recent years. At the same time, the gas delivery infrastructure is rapidly aging, and thus ensuring natural gas infrastructure reliability is becoming one of the critical needs for the industry. The largest component of the natural gas infrastructure is thousands of miles of delivery pipeline networks. The safe operation of these pipelines is of significant importance due to the intrinsic characteristics of hydrocarbons such as toxicity, flammability and explosion velocity. Therefore, the reliable and timely detection of failure of any part of the pipeline is critical to ensure the reliability and safety of the pipelines.

There are a variety of methods that can detect natural gas pipeline leaks, ranging from manual inspection to advanced satellite-based hyperspectral imaging. The variety of methods can be classified into three major categories, i.e., automated detection, semi-automated detection, and manual detection. The automated detection can detect gas leaks by using fixed-location sensors without human operator after installation. However, the fixed location sensors usually have a limited battery life or require electrical supply from an external power source and thus are cost-inefficient and inconvenient for maintenance. The semi-automated detection needs a certain input to perform some task in order to detect the leakage. For example, flyovers are frequently carried out to confirm the location of leaks, but they are not sensitive to small gas leaks due to the distance from the pipeline and short dwell time on any given location. Manual inspection such as walk-throughs requires a human operator to manually measure or observe gas leaks with handheld equipment. Manual inspection is cumbersome, labor-intensive, time-consuming, and is not always feasible due to climatic and landscape conditions. The present invention aims to solve some of these problems by disclosing a leakage detection system for pipelines which is simpler, less expensive and more reliable, and requires less maintenance than the existing gas leak detection systems.

DETAIL DESCRIPTIONS OF THE INVENTION

All illustrations of the drawings are for the purpose of describing selected versions of the present invention and are not intended to limit the scope of the present invention.

The present invention is a system and method of detecting gas-leakage along an underground pipeline system. More specifically, the present invention detects gas leaks for natural gas pipelines. Moreover, the present invention locates a gas leak along an underground pipeline without the need for global positioning system (GPS) devices. The present invention utilizes existing stack vents of an underground pipeline system to accurately determine the presence of a gas leak. The present invention also utilizes renewable energy sources and reduces energy consumption and cost. Thus, the physical system used to implement the method for the present invention includes at least one underground pipeline (Step A), a plurality of sensor units, and at least one remote server (Step B), seen in FIG. 1, FIG. 2, and FIG. 3.

Figure 2:
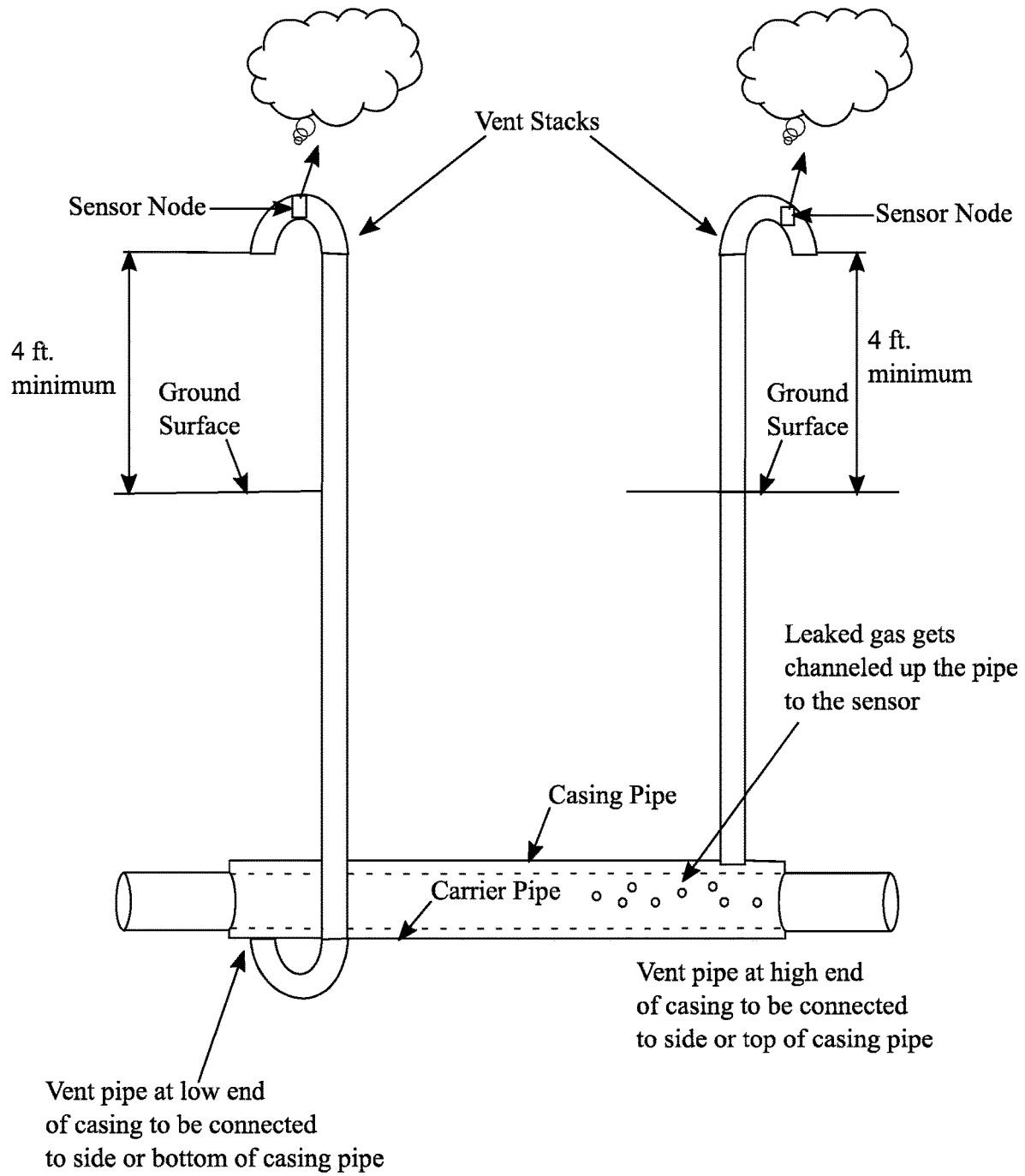
FIG. 2 is a schematic diagram illustrating a plurality of stack vents attached to a casing for an underground pipeline for a method of the present invention.
Figure 3:
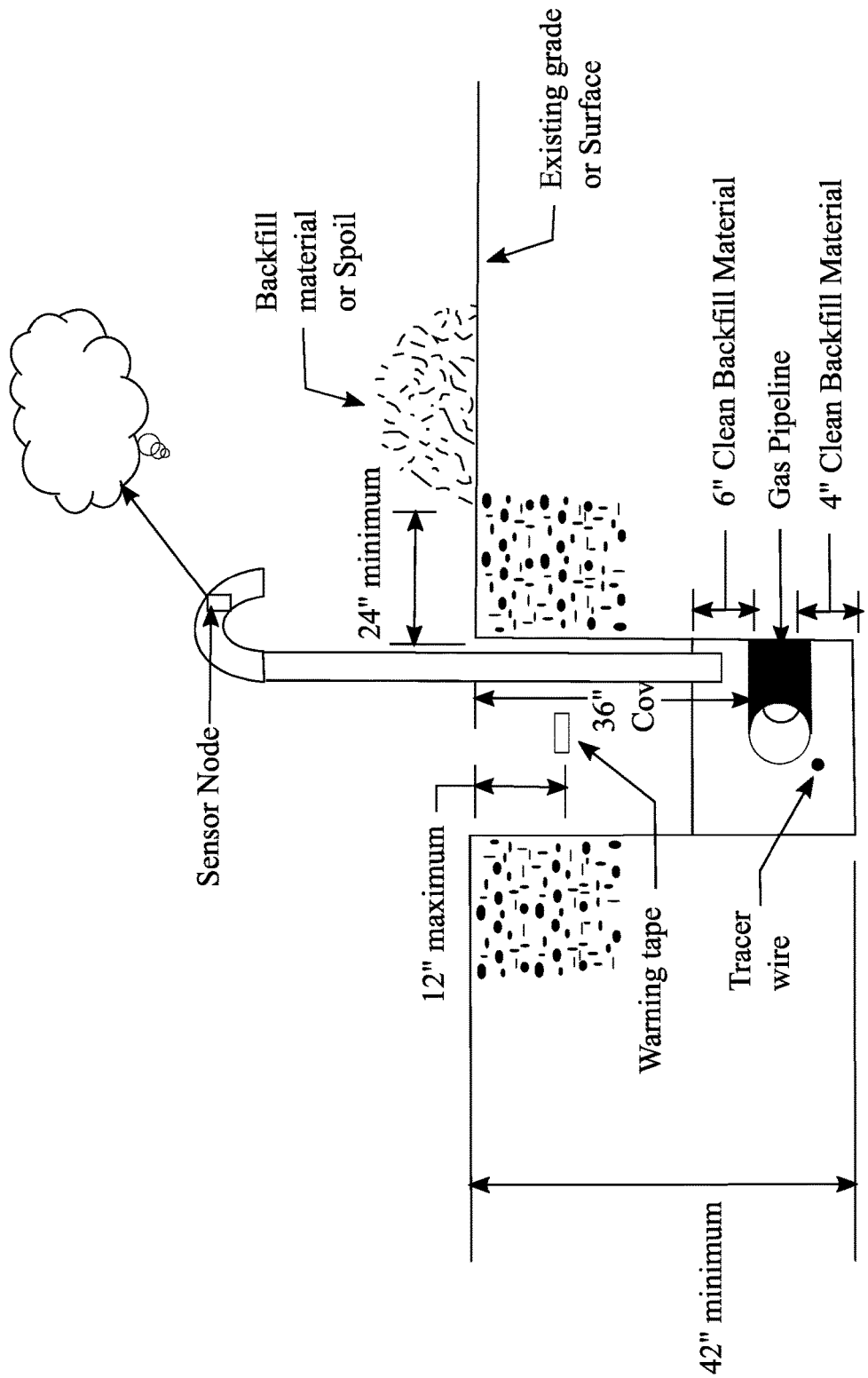
FIG. 3 is a schematic diagram illustrating a specific stack vent installed within a pipeline bed for an underground pipeline for the method of the present invention.

The underground pipeline delivers natural gas to residential, commercial, and public, and industrial areas. Each underground pipeline is a complex infrastructure that connects multiple areas or regions. A plurality of stack vents is in fluid communication with at least one underground pipeline. The plurality of stack vents is a safety measure for the underground pipeline which release any gas from the underground pipeline that may cause an explosion. Each of the plurality of stack vents are strategically positioned along the underground pipeline that traverse under a road crossing, a stream, a river, or any other high-consequence areas that lead into a city. Each sensor unit is mounted within a corresponding stack vent from the plurality of stack vents. Each of the plurality of stack vents therefore also serve to house and protect a corresponding sensor unit from the elements of the surrounding environment. As seen in FIG. 2 and FIG. 3, each of the plurality of stack vents includes an upside down J-shaped outlet that releases the gas from the underground pipeline in order to prevent an explosion. Each sensor unit is mounted within the upside down J-shaped outlet of the corresponding stack vent or is mounted adjacent to the upside down J-shaped outlet of the corresponding stack vent depending on the conditions of the surrounding environment. Alternatively, each of the plurality of stack vents includes an upside down V-shaped outlet that also releases the gas from the underground pipeline in order to prevent an explosion. Each sensor unit is mounted within the upside down V-shaped outlet of the corresponding stack vent or is mounted adjacent to the upside down V-shaped outlet of the corresponding stack vent.

The plurality of stack vents is preferably attached to a casing around the underground pipeline, seen in FIG. 2. The casing is required to protect the underground pipeline positioned under a road crossing or a railroad. Each stack vent is embedded into the casing in order to provide relief of a gas leak along the underground pipeline to the ground surface through each stack vent. Alternatively, the pipeline does not have a casing and the plurality of stack vents are installed offset and above the underground pipeline in a trench or pipeline bed, as seen in FIG. 3. The pipeline bed, along with the plurality of stack vents, serve as a conduit for gas leaks. The gravel, sand, and dirt that make up the pipeline bed are loose and more porous for gas leaks to travel through than through hard soil above and below the pipeline bed. Consequently, the gas leak travels along the pipeline bed and through an available stack vent of the plurality of stacked vents. In both variations of stack vent installation with an underground pipeline, the gas leak travels through a stack vent and past a corresponding sensor unit.

Figure 1:
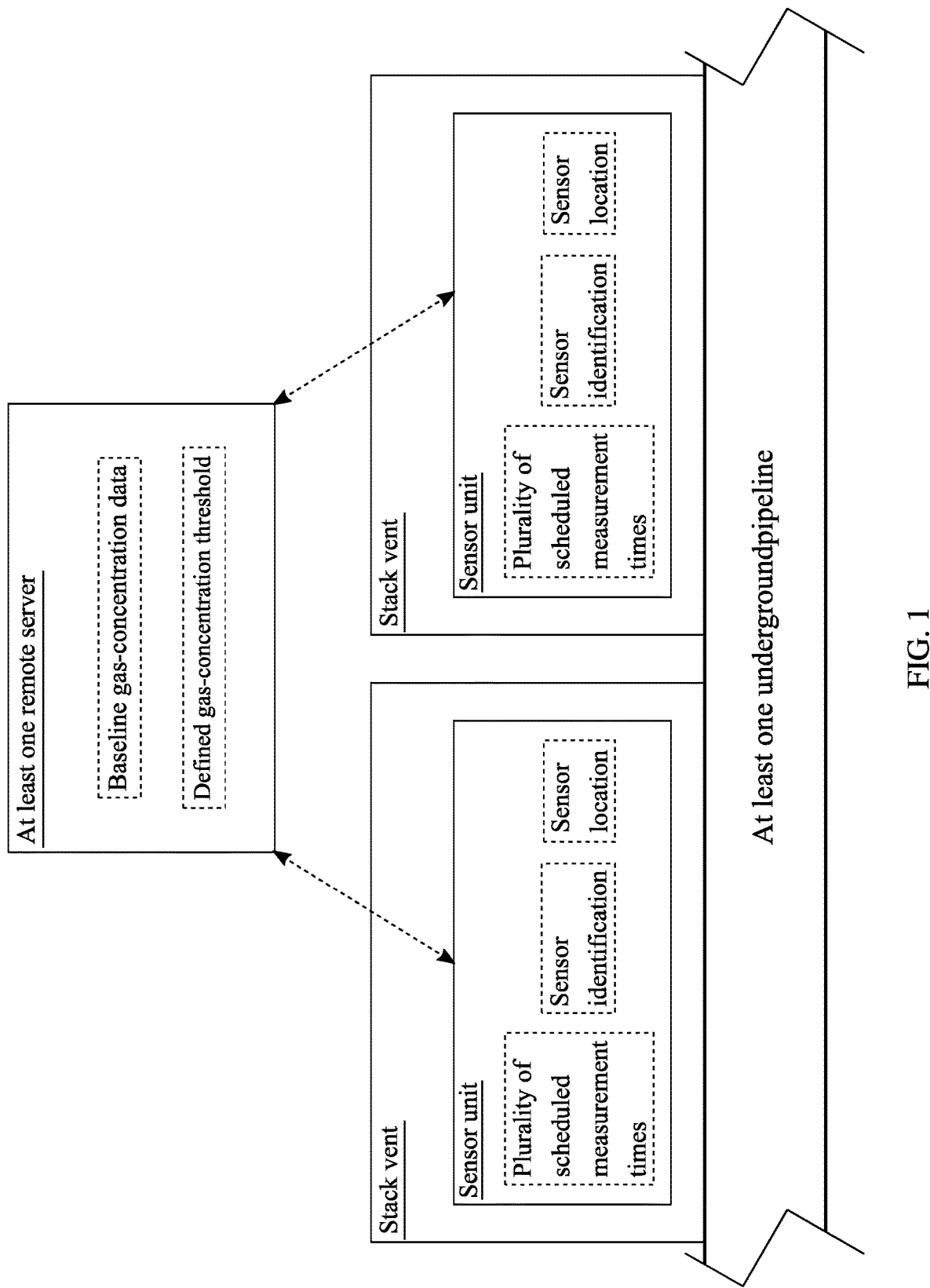
FIG. 1 is a block diagram illustrating the system of the present invention.
Figure 4:
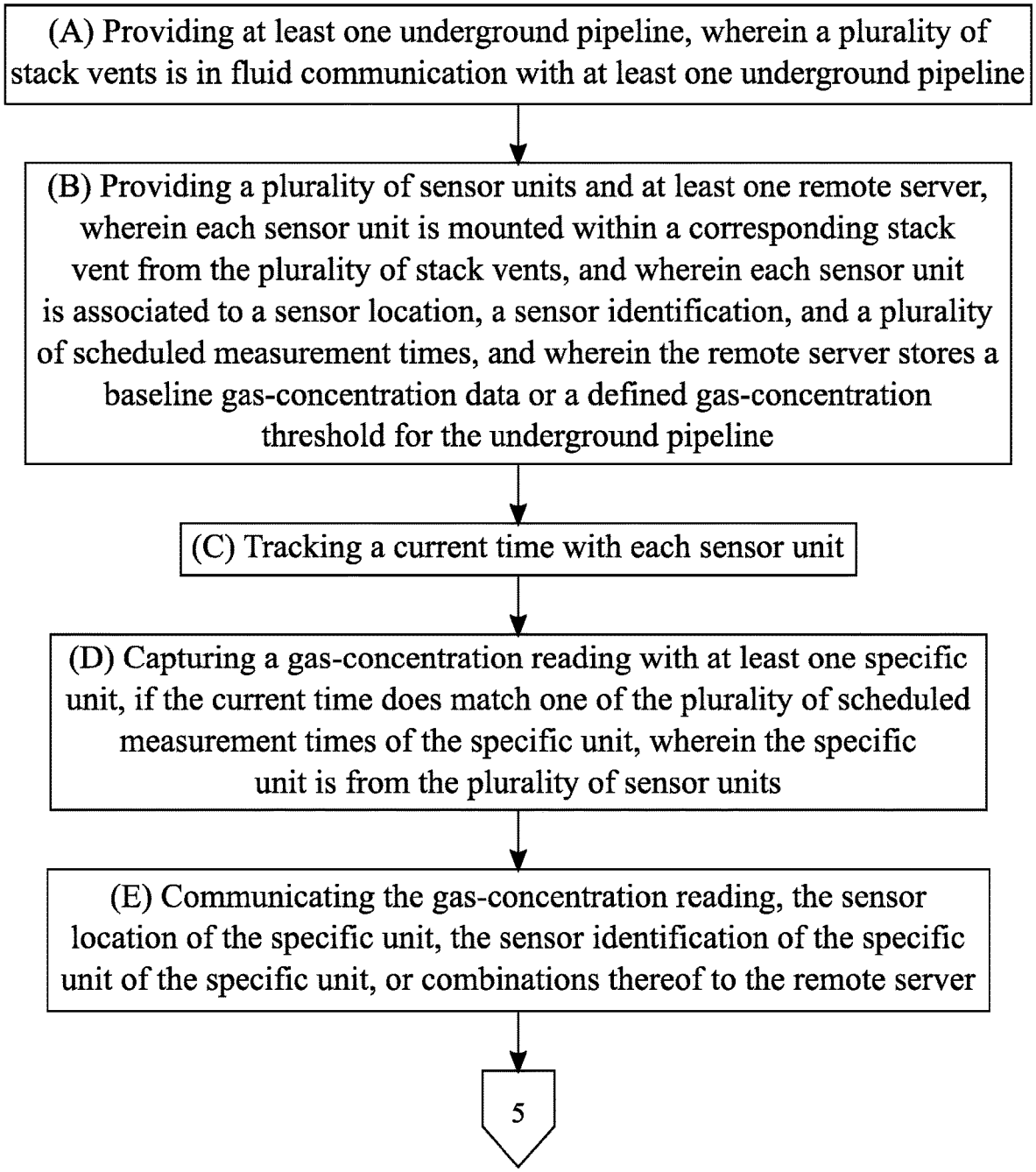
FIG. 4 is a flowchart illustrating the overall process for the method of the present invention.

Each sensor unit identifiable as each sensor unit is associated to a sensor location, a sensor identification, and a plurality of scheduled measurement times, seen in FIG. 1 and FIG. 4. The remote server manages the plurality of sensor units and stores a baseline gas-concentration data or a defined gas-concentration threshold for the underground pipeline. The sensor location is a set of coordinates of the corresponding sensor unit that provide an exact location of the sensor unit, more specifically, the location of the sensor unit along the underground pipeline. The sensor identification differentiates each sensor unit from each other so that each sensor location and any gas measurements detected with a sensor unit is able to be associated with the corresponding sensor unit. The plurality of scheduled measurement times turns on and turns off its corresponding sensor unit in order to conserve power. Alternatively, if sufficient power is identified and provided by a power source, such as a battery, the plurality of sensor units may remain turned on until a minimum power supply percentage is reached. The baseline gas-concentration data is an accumulation of gas-concentration data in normal circumstances without a gas leak. The defined gas-concentration threshold for the underground pipeline is the comparable standard for a gas concentration in the air that is considered a gas leak for each type of environment around a stack vent and type of installation of a stack vent.

Figure 5:
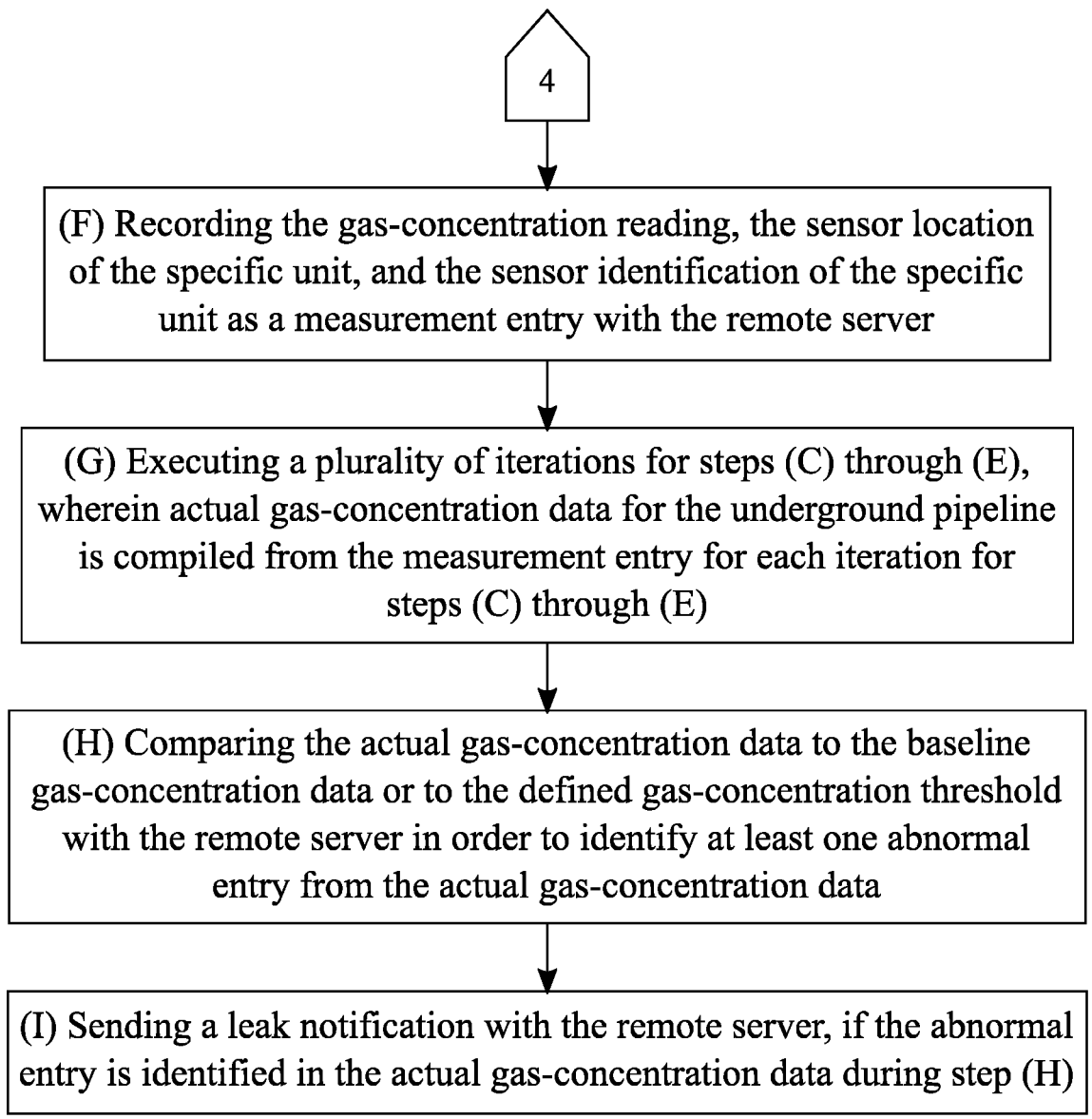
FIG. 5 is a continuation of the flowchart in FIG. 3.

The overall process for the method of the present invention includes the following steps that are implemented amongst the at least one underground pipeline, the plurality of stack vents, the plurality of sensor units, and the at least one remote server. The overall process begins by tracking a current time with each sensor unit (Step C), shown in FIG. 4. The current time determines which sensor unit remains turned on and turned off according to the plurality of scheduled measurement times. The current time also accurately timestamps a measurement reading from each sensor unit when detecting a gas-leak. A gas-concentration reading is then captured with at least one specific unit, if the current time does match one of the plurality of scheduled measurement times of the specific unit (Step D). More specifically, the specific unit is from the plurality of sensor units. The gas-concentration reading provides a level of a gas detected by the at least one specific unit from the underground pipeline. In order to identify the gas-concentration reading as a gas leak, the gas-concentration reading, the sensor location of the specific unit, the sensor identification of the specific unit from the specific unit, or combinations thereof is communicated to the remote server (Step E). As seen in FIG. 5, the gas-concentration reading, the sensor location of the specific unit, and the sensor identification of the specific unit is recorded as a measurement entry with the remote server (Step F), thereby associating the gas-concentration reading with the specific unit. The duration and the intensity of the gas leak is determined as the plurality of iterations for Step C through Step E are executed, wherein actual gas-concentration data for the underground pipeline is compiled from the measurement entry for each iteration for Step C through Step E (Step G). The actual gas-concentration data is compared to the baseline gas-concentration data or to the defined gas-concentration threshold with the remote server in order to identify at least one abnormal entry from the actual gas-concentration data (Step H). An abnormal entry from the actual gas-concentration data is any entry indicating a notable increase in gas concentration, which in turn indicates a data associated with a gas leak from the underground pipeline. A leak notification is sent with the remote server, if the abnormal entry is identified in the actual gas-concentration data during Step H (Step I) so that an operator or verified official may quickly respond to the gas leak.

Figure 6:
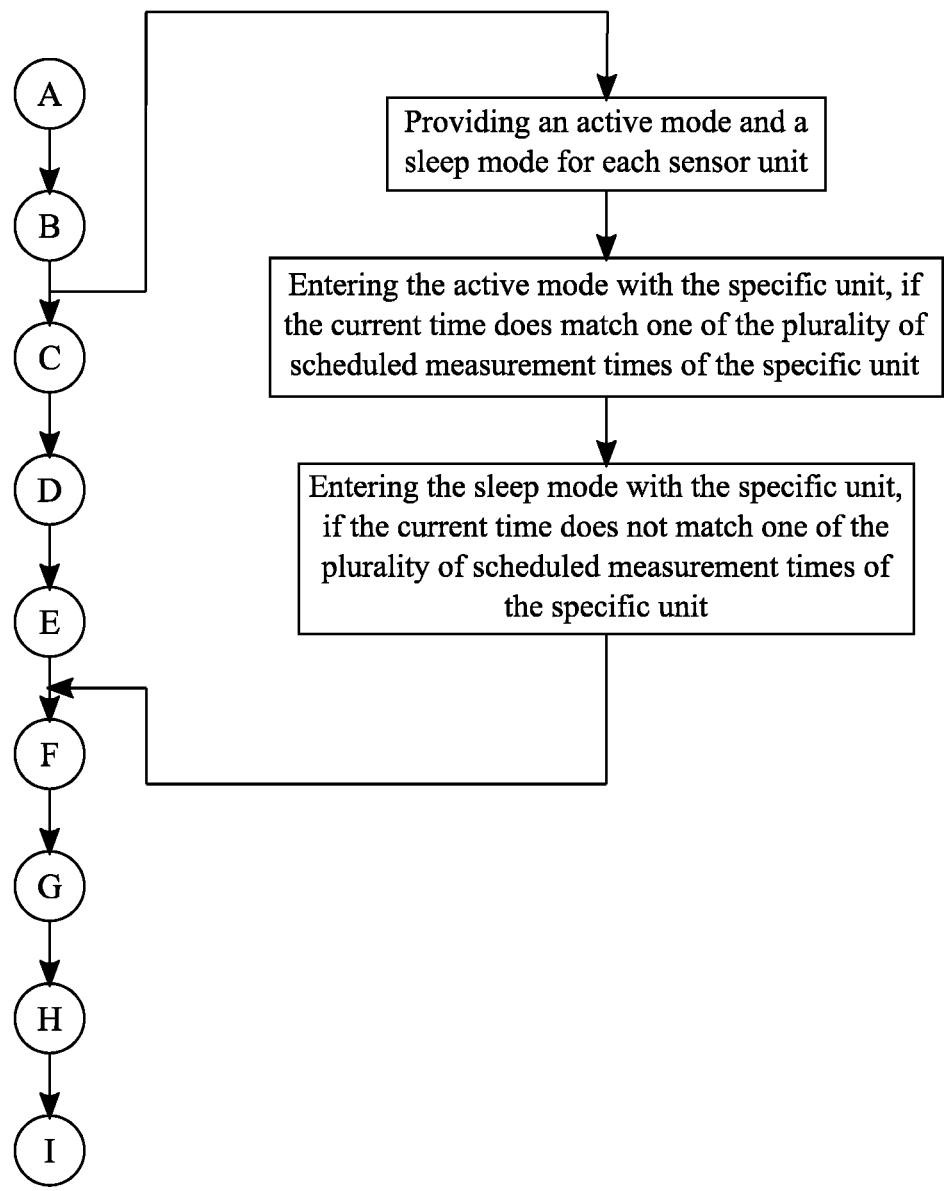
FIG. 6 is a flowchart illustrating the subprocess for entering an active mode or a sleep mode with a specific unit of the plurality of sensor units.

In order for the present invention to independently turn off or on each of the plurality of sensor units, an active mode and a sleep mode is provided for each sensor unit, seen in FIG. 6. Each sensor unit is either in the active mode or in the sleep mode based on their scheduled measurement times. The active mode turns on the specific unit to capture a gas-concentration reading, and the sleep mode turns off the specific unit at any other times. Thus, the specific unit enters the active mode, if the current time does match one of the plurality of scheduled measurement times of the specific unit. Likewise, the specific unit enters the sleep mode, if the current time does not match one of the plurality of scheduled measurement times of the specific unit.

Figure 7:
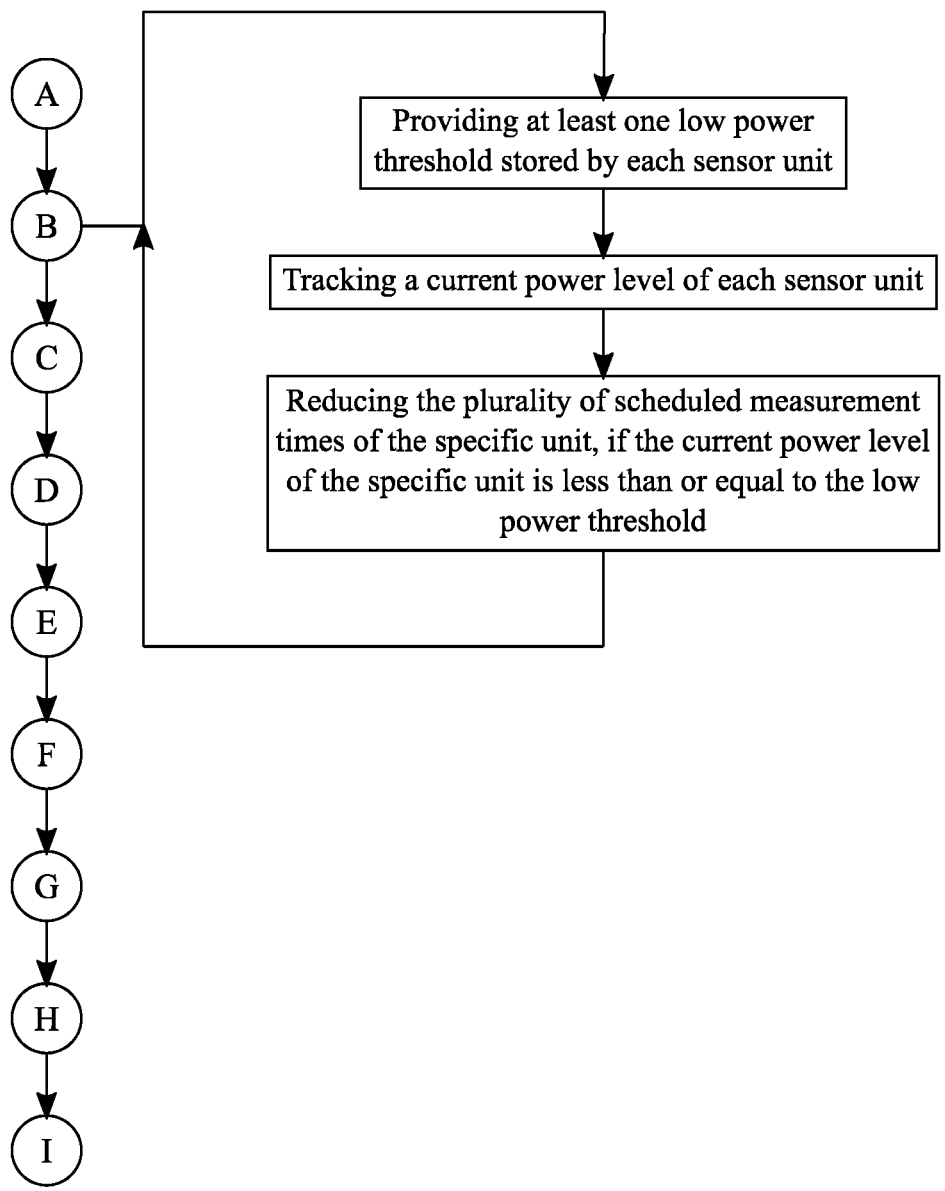
FIG. 7 is a flowchart illustrating the subprocess for reducing the plurality of scheduled measurement times of a specific unit of the plurality of sensor units based on at least one low power threshold.

The present invention further preserves energy as at least one low power threshold is stored by each sensor unit, seen in FIG. 7. The at least one low power threshold is a minimum amount of available power that determines if the duration of the active mode and the frequency of scheduled measurement times. A current power level of each sensor unit is tracked in order to monitor if each sensor unit is functioning with a normal power level. The current power level is the amount of power available for each sensor unit in real-time. In order to preserve the remaining power for a sensor unit with a low power level, the plurality of scheduled measurement times of the specific unit is reduced, if the current power level of the specific unit is less than or equal to the low power threshold.

Figure 8:
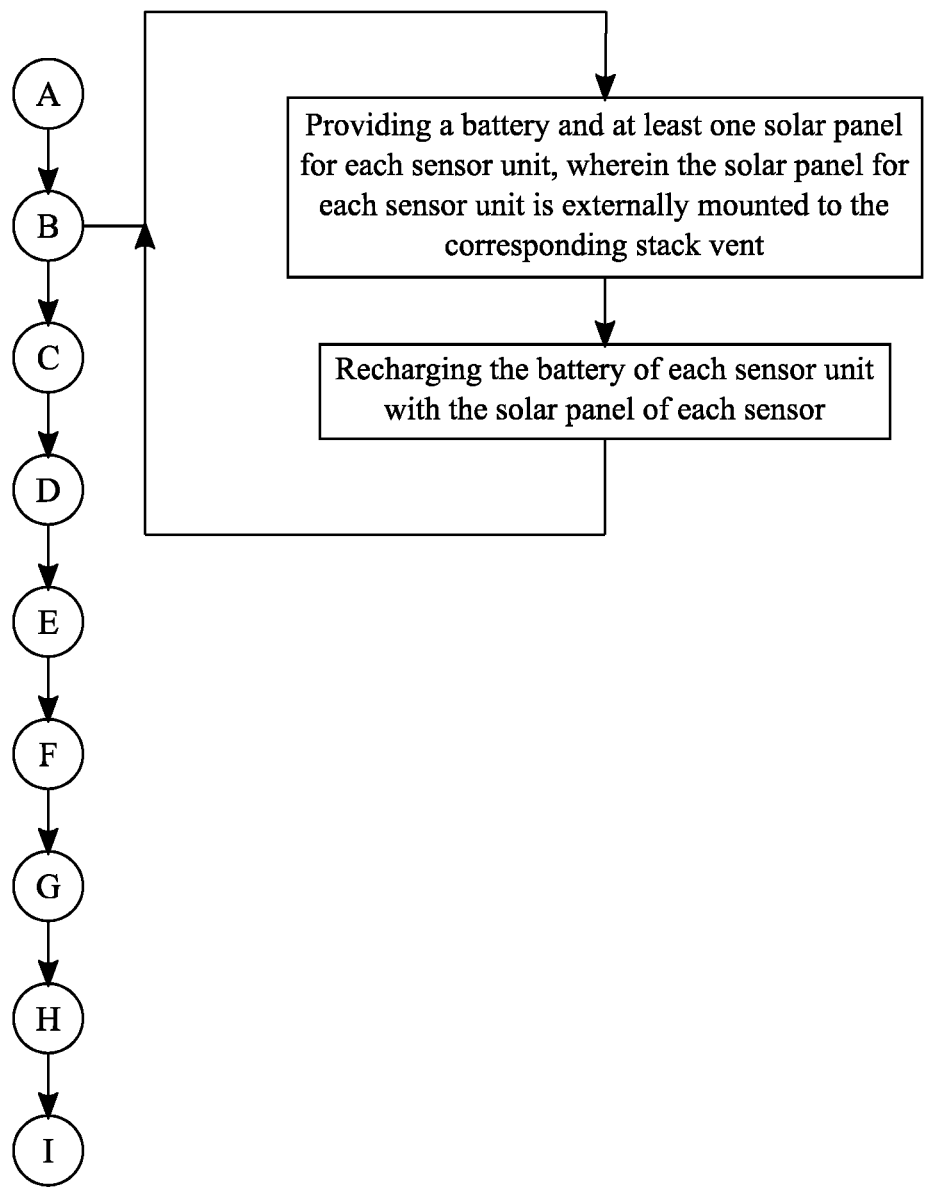
FIG. 8 is a flowchart illustrating the subprocess for recharging a battery of each sensor unit with a solar panel of each sensor.
Figure 9:
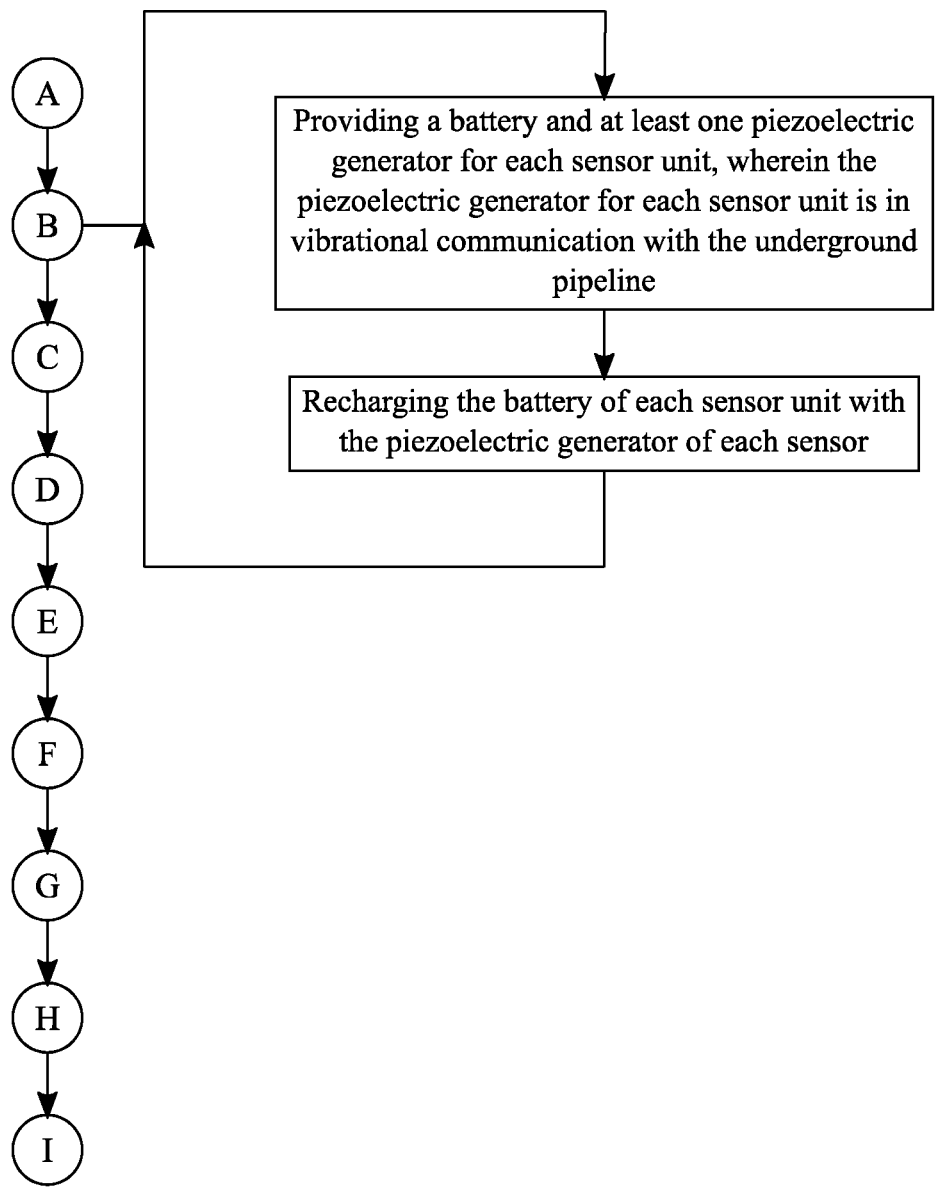
FIG. 9 is a flowchart illustrating the subprocess for recharging a battery of each sensor unit with a piezoelectric generator of each sensor unit.

As seen in FIG. 8, power is supplied to each sensor unit with renewable sources of energy as a battery and at least one solar panel is provided for each sensor unit, wherein the solar panel for each sensor unit is externally mounted to the corresponding stack vent. The battery is the power supply for each sensor unit, and the at least one solar panel harnesses and converts renewable energy from the sun. The battery of each sensor unit is recharged with the solar panel of each sensor, thereby efficiently replenishing the power supply for each sensor unit when needed. Alternatively, at least one piezoelectric generator is provided for each sensor unit, wherein the piezoelectric generator for each sensor unit is vibrational communication with the underground pipeline, as seen in FIG. 9. The at least one piezoelectric generator harnesses and converts the kinetic energy from the shocks and vibrations underground around the underground pipeline. The battery of each sensor unit is recharged with the piezoelectric generator of each sensor, thereby efficiently replenishing the power supply for each sensor unit when needed.

Figure 10:
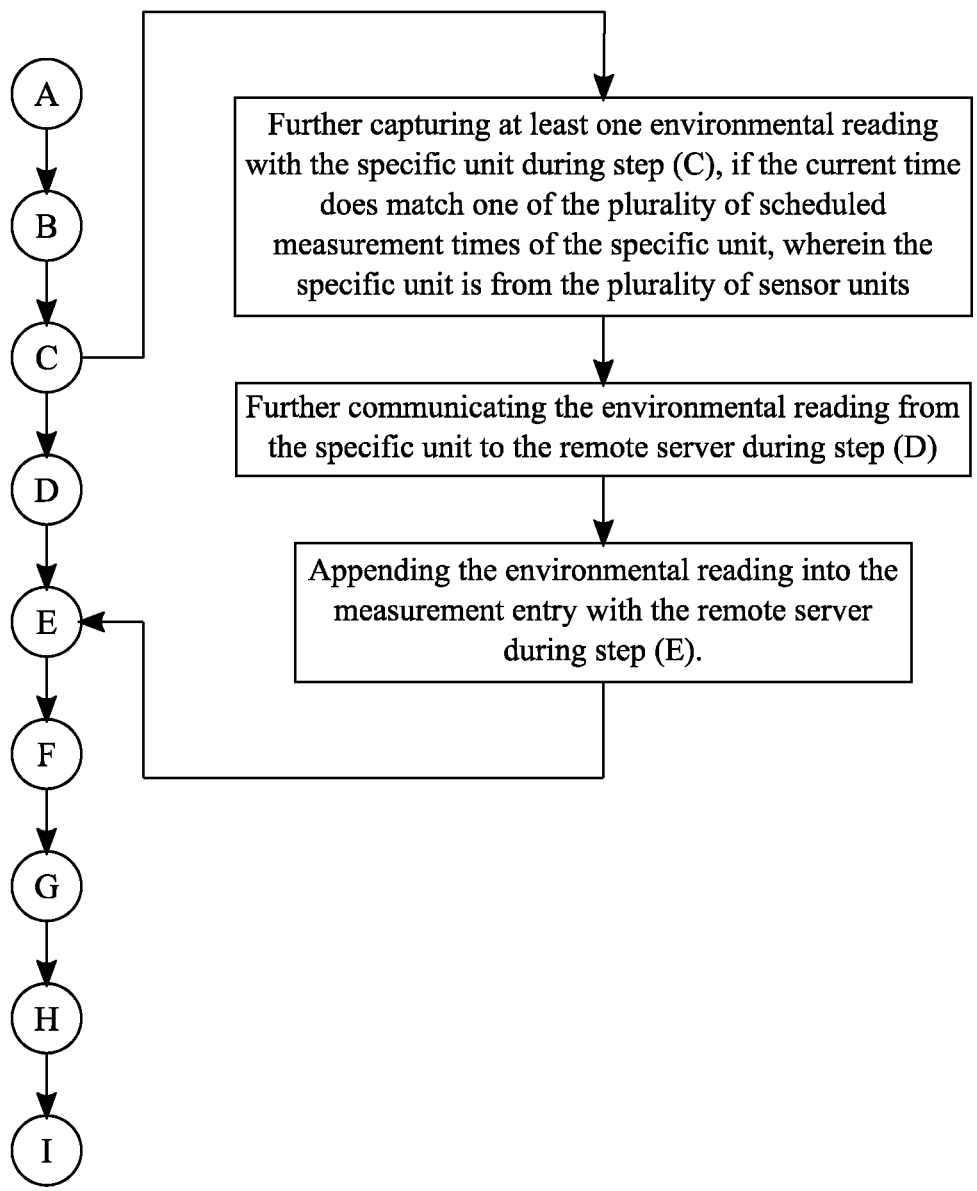
FIG. 10 is a flowchart illustrating the subprocess for capturing at least one environmental reading with a specific unit and appending the environmental reading into the measurement entry.

The present invention accurately determines the presence of gas-leakage as at least one environmental reading is further captured with the specific unit during Step C, if the current time does match one of the plurality of scheduled measurement times of the specific unit, seen in FIG. 10. The at least one environmental reading may include, but is not limited to, a temperature reading and a humidity reading and accounts for any inaccuracies in the gas-concentration reading. The environmental reading from the specific unit is further communicated to the remote server during Step D and is appended into the measurement entry with the remote server during Step E in order to take into account any environmental factors that may influence the identification of a gas leak.

Figure 11:
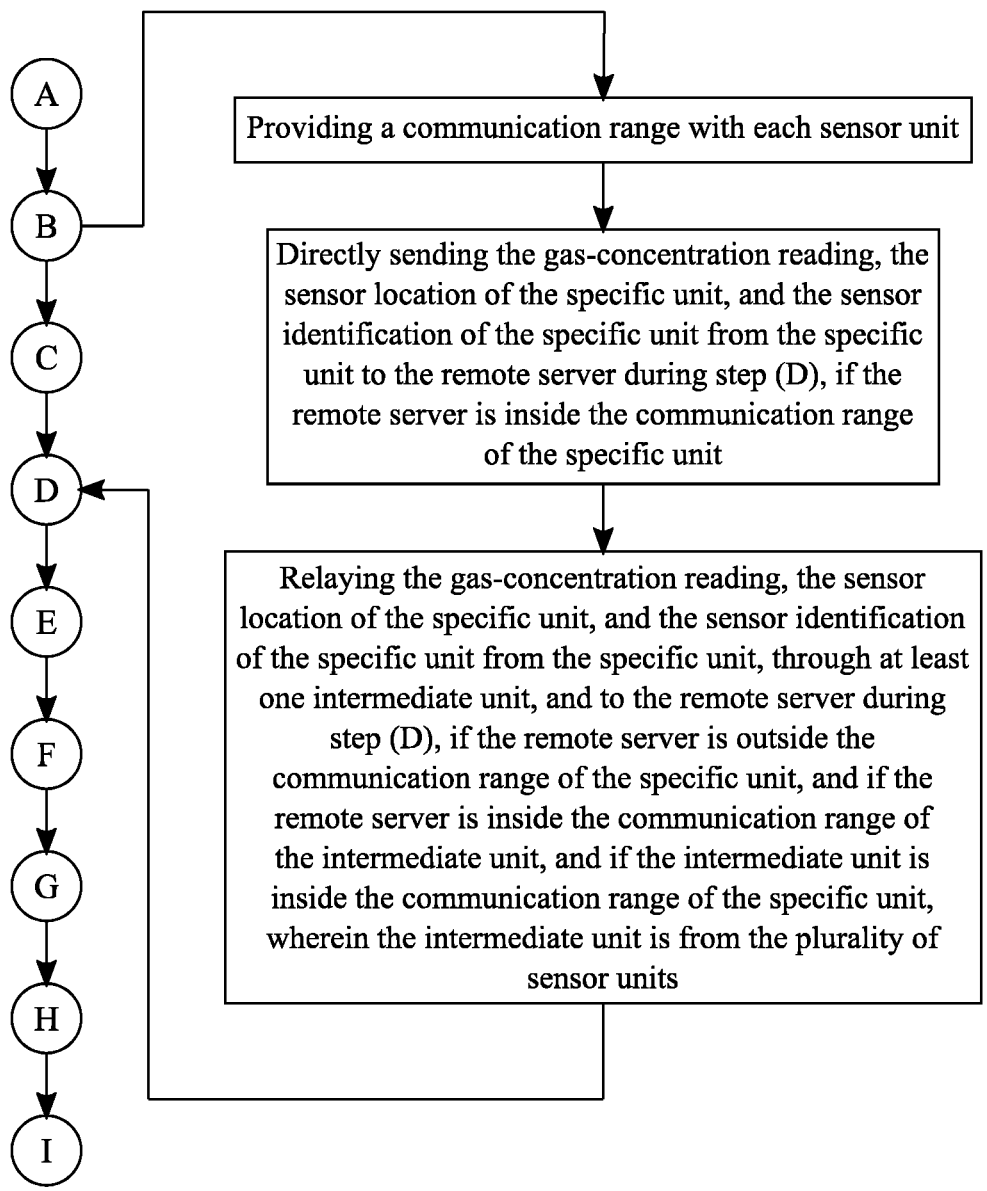
FIG. 11 is a flowchart illustrating the subprocess for relaying a gas-concentration reading, a sensor location of a specific unit, and a sensor identification of the specific unit from the specific unit, through at least one intermediate sensor unit, and to a remote server.

In order to receive the gas-concentration reading from a specific unit, a communication range is provided with each sensor unit, seen in FIG. 11. The communication range is a defined area for each sensor unit that allows a sensor unit to communicate with another device. In order to make sure that the remote server is able to communicate with each sensor unit, the gas-concentration reading, the sensor location of the specific unit, and the sensor identification of the specific unit is directly sent from the specific unit to the remote server during Step D, if the remote server is inside the communication range of the specific unit. Alternatively, the sensor location of the specific unit, and the sensor identification of the specific unit is relayed from the specific unit, through at least one intermediate unit, and to the remote server during Step D, if the remote server is outside the communication range of the specific unit, if the remote server is inside the communication range of the intermediate unit, and if the intermediate unit is inside the communication range of the specific unit, wherein the immediate unit is from the plurality of sensor units. The at least one intermediate unit is typically a neighboring sensor unit within the communication range of the specific unit.

Figure 12:
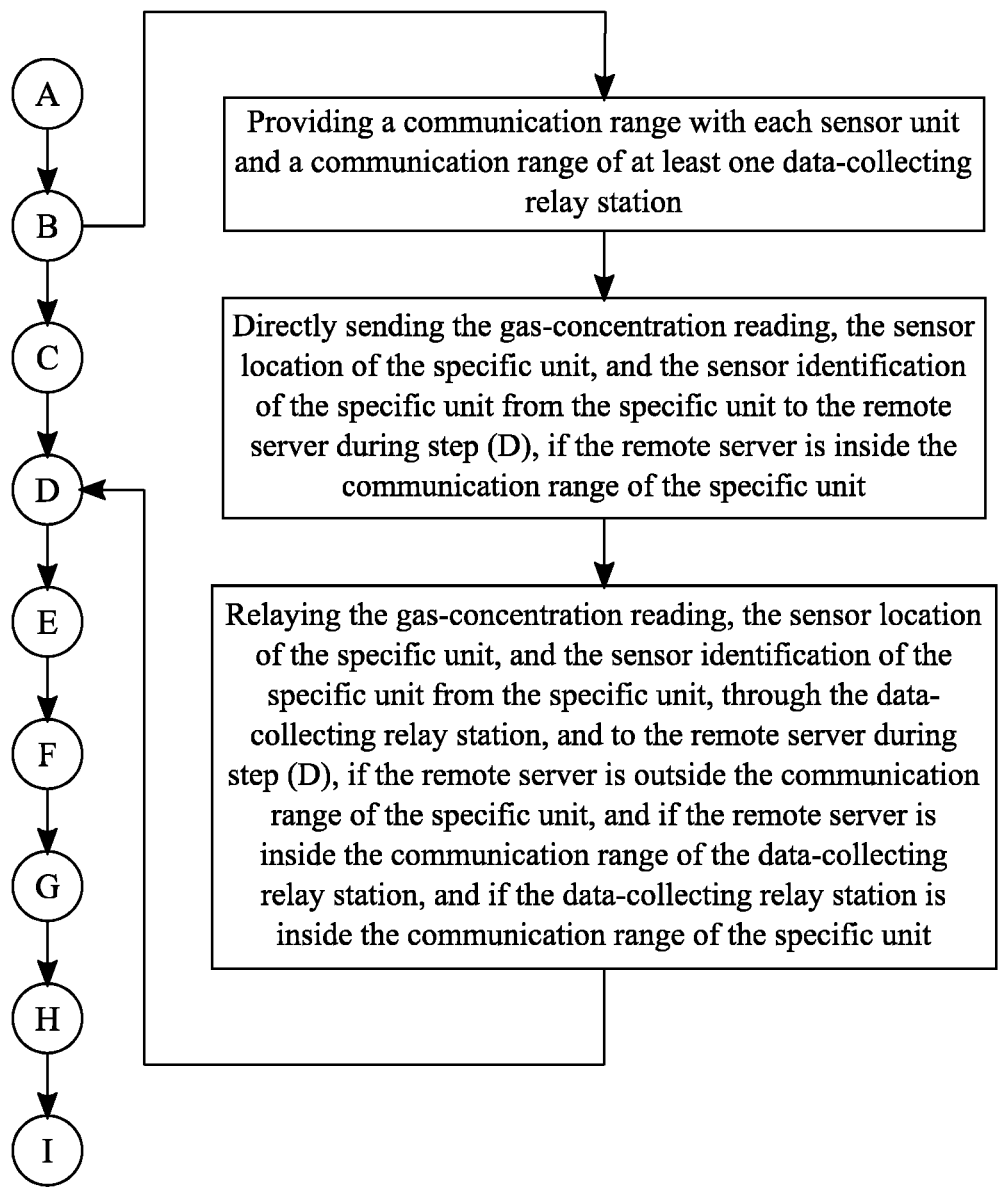
FIG. 12 is a flowchart illustrating the subprocess for relaying a gas-concentration reading, a sensor location of a specific unit, and a sensor identification of the specific unit from the specific unit, through a data-collecting relay station, and to the remote server.

Similarly, a communication range of at least one data-collecting relay station is further provided in order to wirelessly connect more sensor units further along a large underground pipeline or neighboring pipelines, seen in FIG. 12. In order to make sure that the remote server is able to communicate with each sensor unit, the sensor location of the specific unit, and the sensor identification of the specific unit is directly sent from the specific unit to the remote server during Step D, if the remote server is inside the communication range of the specific unit. Alternatively, the gas-concentration reading, the sensor location of the specific unit, and the sensor identification of the specific unit is relayed from the specific unit, through the data-collecting relay station, and to the remote server during Step D, if the remote server is outside the communication range of the specific unit, if the remote server is outside the communication range of the specific unit, and if the remote server is inside the communication range of the data-collecting relay station, and if the data-collecting relay station is inside the communication range of the specific unit. The data-collecting relay station is typically a hub to collect, store, and eventually relay data that is captured from sensor units in very remote locations along the underground pipeline.

Figure 13:
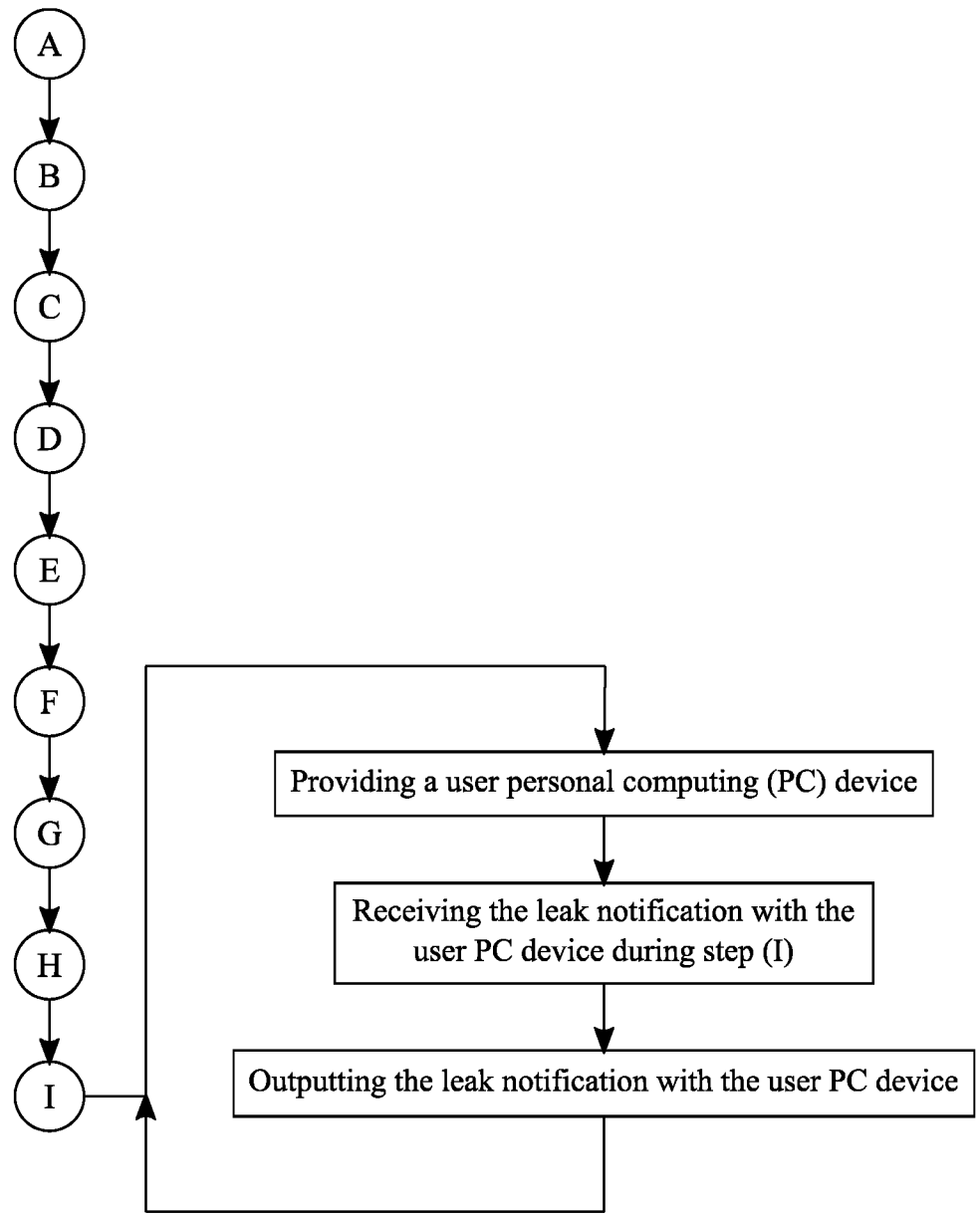
FIG. 13 is a flowchart illustrating the subprocess for outputting a leak notification with a user personal computing (PC) device.
Figure 14:
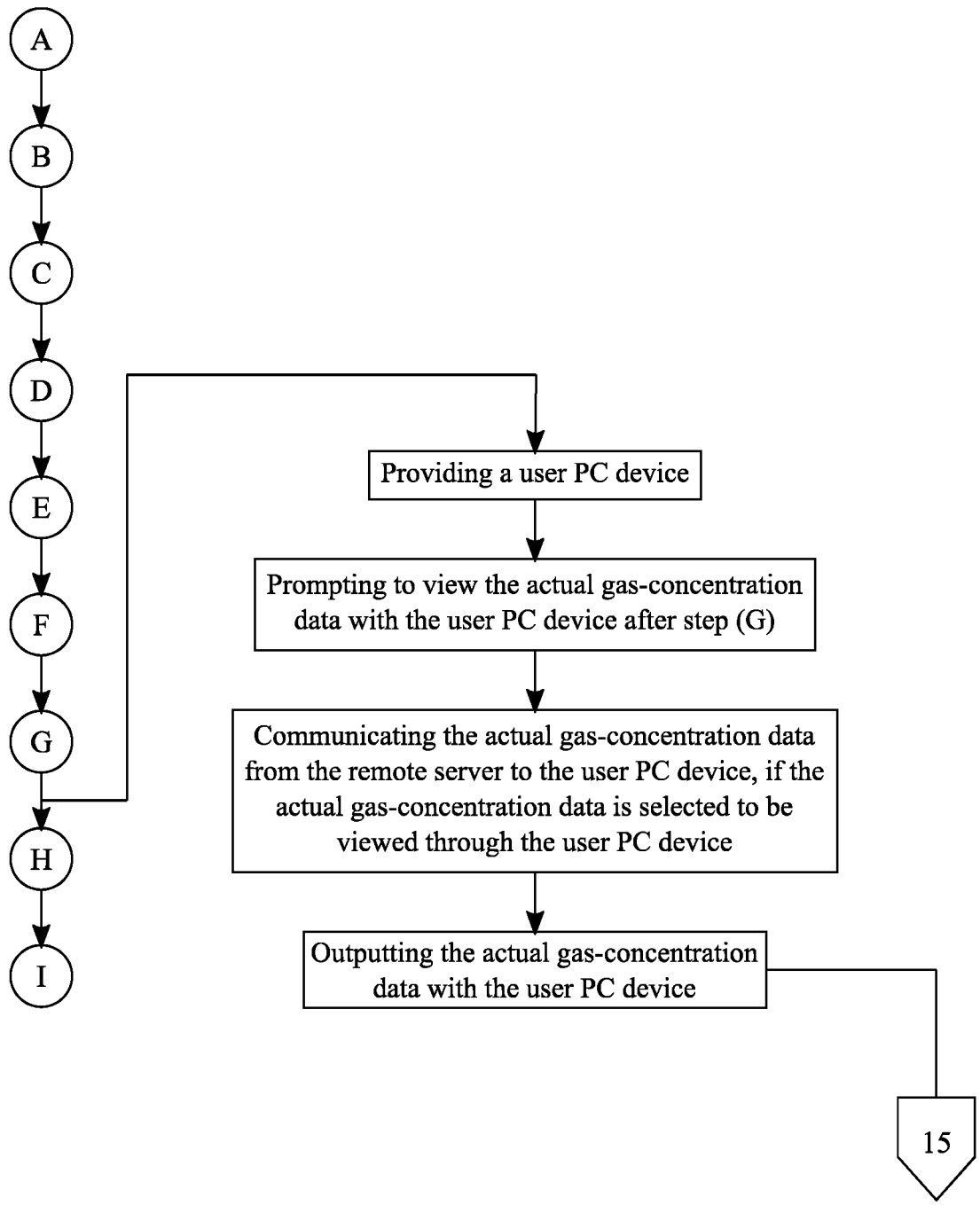
FIG. 14 is a flowchart illustrating the subprocess for outputting the actual gas-concentration data with a user PC device.
Figure 15:
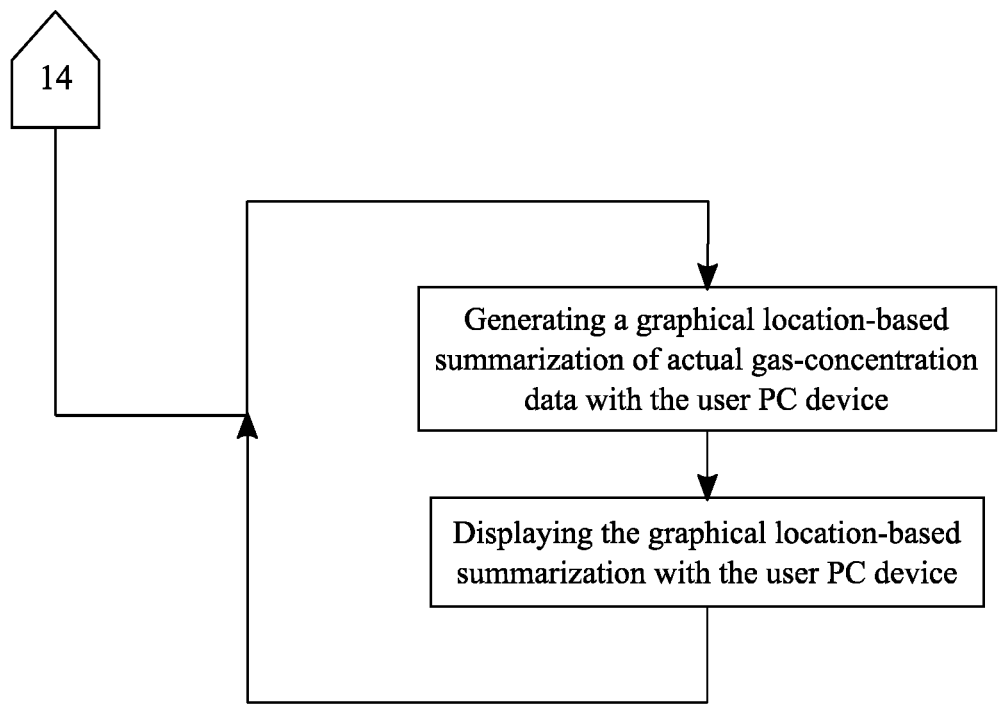
FIG. 15 is a flowchart illustrating the subprocess for displaying a graphical location-based summarization with the user PC device.

In order for an operator to respond to a gas leak, a user personal computing (PC) device is provided, as seen in FIG. 13. The user PC device allows the operator to interact with the present invention. The user PC device may be, but is not limited to, a desktop, a laptop, a tablet PC, a computerized mobile phone, or a computerized watch. The leak notification is received with the user PC device during Step I and is outputted with the user PC device. The leak notification may be outputted with a visual alert and an audio alert. In order to view the gas-concentration data, the user is prompted to view the actual gas-concentration data with the user PC device after Step G, as seen in FIG. 14. The actual gas-concentration data is communicated from the remote server to the user PC device, if the actual gas-concentration data is selected to be viewed through the user PC device. The actual gas-concentration data is outputted with the user PC device so that the user can review the actual gas-concentration data in its entirety and manually identify abnormalities in the actual gas-concentration data. In further embodiments of the present invention, the plurality of sensor units may be viewed along the entirety of at least one underground pipeline. Seen in FIG. 15, a graphical location-based summarization of the actual gas-concentration data is generated with the user PC device. The graphical location-based summarization of the actual gas-concentration data is preferably a map with each sensor node positioned along the underground pipeline according to the sensor location of each sensor node. The graphical location-based summarization is displayed with the user PC device. Preferably, a symbol represents each sensor node. Furthermore, the actual gas-concentration data may automatically be presented beside the corresponding sensor node such as the gas-concentration reading.

Although the invention has been explained in relation to its preferred embodiment, it is to be understood that many other possible modifications and variations can be made without departing from the spirit and scope of the invention as hereinafter claimed.

What is claimed is:

1. A method of detecting gas-leakage along an underground pipeline system, the method comprises the steps of:
   (A) providing at least one underground pipeline, wherein a plurality of stack vents is in fluid communication with at least one underground pipeline;
   (B) providing a plurality of sensor units and at least one remote server, wherein each sensor unit is mounted within a corresponding stack vent from the plurality of stack vents, and wherein each sensor unit is associated to a sensor location, a sensor identification, and a plurality of scheduled measurement times, and wherein the remote server stores a baseline gas-concentration data or a defined gas-concentration threshold for the underground pipeline;
(C) tracking a current time with each sensor unit;
(D) capturing a gas-concentration reading with at least one specific unit, if the current time does match one of the plurality of scheduled measurement times of the specific unit, wherein the specific unit is from the plurality of sensor units;
(E) communicating the gas-concentration reading, the sensor location of the specific unit, the sensor identification of the specific unit of the specific unit, or combinations thereof to the remote server;
(F) recording the gas-concentration reading, the sensor location of the specific unit, and the sensor identification of the specific unit as a measurement entry with the remote server;
(G) executing a plurality of iterations for steps (C) through (E), wherein actual gas-concentration data for the underground pipeline is compiled from the measurement entry for each iteration for steps (C) through (E);
(H) comparing the actual gas-concentration data to the baseline gas-concentration data or to the defined gas-concentration threshold with the remote server in order to identify at least one abnormal entry from the actual gas-concentration data; and,
(I) sending a leak notification with the remote server, if the abnormal entry is identified in the actual gas-concentration data during step (H).

2. The method of detecting gas-leakage along an underground pipeline system, the method as claimed in claim 1 comprises the steps of:
providing an active mode and a sleep mode for each sensor unit;
entering the active mode with the specific unit, if the current time does match one of the plurality of scheduled measurement times of the specific unit; and,
entering the sleep mode with the specific unit, if the current time does not match one of the plurality of scheduled measurement times of the specific unit.

3. The method of detecting gas-leakage along an underground pipeline system, the method as claimed in claim 1 comprises the steps of:
providing at least one low power threshold stored by each sensor unit;
tracking a current power level of each sensor unit; and,
reducing the plurality of scheduled measurement times of the specific unit, if the current power level of the specific unit is less than or equal to the low power threshold.

4. The method of detecting gas-leakage along an underground pipeline system, the method as claimed in claim 1 comprises the steps of:
providing a battery and at least one solar panel for each sensor unit, wherein the solar panel for each sensor unit is externally mounted to the corresponding stack vent; and,
recharging the battery of each sensor unit with the solar panel of each sensor.

5. The method of detecting gas-leakage along an underground pipeline system, the method as claimed in claim 1 comprises the steps of:
providing a battery and at least one piezoelectric generator for each sensor unit, wherein the piezoelectric generator for each sensor unit is in vibrational communication with the underground pipeline;
recharging the battery of each sensor unit with the piezoelectric generator of each sensor.

6. The method of detecting gas-leakage along an underground pipeline system, the method as claimed in claim 1 comprises the steps of:
further capturing at least one environmental reading with the specific unit during step (C), if the current time does match one of the plurality of scheduled measurement times of the specific unit;
further communicating the environmental reading from the specific unit to the remote server during step (D); and,
appending the environmental reading into the measurement entry with the remote server during step (E).

7. The method of detecting gas-leakage along an underground pipeline system, the method as claimed in claim 1 comprises the steps of:
providing a communication range with each sensor unit;
directly sending the gas-concentration reading, the sensor location of the specific unit, and the sensor identification of the specific unit from the specific unit to the remote server during step (D), if the remote server is inside the communication range of the specific unit; and,
relaying the gas-concentration reading, the sensor location of the specific unit, and the sensor identification of the specific unit from the specific unit, through at least one intermediate unit, and to the remote server during step (D), if the remote server is outside the communication range of the specific unit, and if the remote server is inside the communication range of the intermediate unit, and if the intermediate unit is inside the communication range of the specific unit, wherein the intermediate unit is from the plurality of sensor units.

8. The method of detecting gas-leakage along an underground pipeline system, the method as claimed in claim 1 comprises the steps of:
providing a communication range with each sensor unit and a communication range of at least one data-collecting relay station;
directly sending the gas-concentration reading, the sensor location of the specific unit, and the sensor identification of the specific unit from the specific unit to the remote server during step (D), if the remote server is inside the communication range of the specific unit; and,
relaying the gas-concentration reading, the sensor location of the specific unit, and the sensor identification of the specific unit from the specific unit, through the data-collecting relay station, and to the remote server during step (D), if the remote server is outside the communication range of the specific unit, and if the remote server is inside the communication range of the data-collecting relay station, and if the data-collecting relay station is inside the communication range of the specific unit.

9. The method of detecting gas-leakage along an underground pipeline system, the method as claimed in claim 1, wherein each of the plurality of stack vents includes an upside down J-shaped outlet, and wherein each sensor unit is mounted within the upside down J-shaped outlet of the corresponding stack vent or is mounted adjacent to the upside down J-shaped outlet of the corresponding stack vent.

10. The method of detecting gas-leakage along an underground pipeline system, the method as claimed in claim 1, wherein each of the plurality of stack vents includes an upside down V-shaped outlet, and wherein each sensor unit is mounted within the upside down V-shaped outlet of the corresponding stack vent or is mounted adjacent to the upside down V-shaped outlet of the corresponding stack vent.

11. The method of detecting gas-leakage along an underground pipeline system, the method as claimed in claim 1 comprises the steps of:
   providing a user personal computing (PC) device;
   receiving the leak notification with the user PC device during step (I); and,
   outputting the leak notification with the user PC device.

12. The method of detecting gas-leakage along an underground pipeline system, the method as claimed in claim 1 comprises the steps of:
   providing a user PC device;
   prompting to view the actual gas-concentration data with the user PC device after step (G);
   communicating the actual gas-concentration data from the remote server to the user PC device, if the actual gas-concentration data is selected to be viewed through the user PC device; and,
   outputting the actual gas-concentration data with the user PC device.

13. The method of detecting gas-leakage along an underground pipeline system, the method as claimed in claim 12 comprises the steps of:
   generating a graphical location-based summarization of actual gas-concentration data with the user PC device; and,
   displaying the graphical location-based summarization with the user PC device.

* * * * *